United States Patent [19]

Hsiao et al.

[11] Patent Number: 4,863,743

[45] Date of Patent: Sep. 5, 1989

[54] CONTROLLED RELEASE POTASSIUM CHLORIDE

[75] Inventors: Charles Hsiao, Cooper City, Fla.; Chi T. Chou, Monsey, N.Y.

[73] Assignee: Key Pharmaceuticals, Inc., Kenilworth, N.J.

[21] Appl. No.: 830,981

[22] Filed: Feb. 19, 1986

Related U.S. Application Data

[63] Continuation-in-part of Ser. No. 702,714, Feb. 19, 1985, abandoned.

[51] Int. Cl.$^4$ ............................ A61K 9/32; A61K 9/36
[52] U.S. Cl. ................................... 424/476; 424/480; 424/482; 424/495; 424/497; 424/498
[58] Field of Search ............... 424/480, 473, 476, 482, 424/495, 497, 498

[56] References Cited

U.S. PATENT DOCUMENTS

| | | | |
|---|---|---|---|
| 3,538,214 | 11/1970 | Polli et al. | 424/473 |
| 4,519,801 | 5/1985 | Edgren | 424/473 |
| 4,553,973 | 11/1985 | Edgren | 424/473 |
| 4,555,399 | 11/1985 | Hsiao | 424/480 |
| 4,629,620 | 12/1986 | Lindahl et al. | 424/473 |
| 4,666,703 | 5/1987 | Kopf | 424/473 |

*Primary Examiner*—Shep K. Rose
*Attorney, Agent, or Firm*—John J. Maitner; Stephen I. Miller; James Nelson

[57] ABSTRACT

A controlled release potassium chloride tablet is disclosed which is comprised of potassium chloride crystals having a mesh size of about 30 to about 50 mesh which are coated with a coating material comprised of ethylcellulose and hydroxypropylcellulose. The coated crystals form micro pellets which then can be compressed into tablets. The tablets disintegrate rapidly in an aqueous environment thus assuring a more uniform dissolution of the active component as compared with other types of controlled release potassium chloride dosage formulations. The distribution of the potassium chloride micro pellets over a wide surface area in the gastrointestinal mucosa aids in reducing the risk of gastrointestinal lesions. The formation of the coated micro pellets which disperse quickly upon contact with aqueous environment allow for the repeated chronic oral administration of a relatively large dose of potassium chloride (20 mEq).

12 Claims, No Drawings

CONTROLLED RELEASE POTASSIUM CHLORIDE

CROSS REFERENCE TO RELATED APPLICATIONS

This application is a continuation-in-part of Ser. No. 702,714, filed Feb. 19, 1985 now abandoned.

FIELD OF THE INVENTION

The present invention relates to a controlled release potassium chloride tablet. More specifically, the present invention relates to a controlled release potassium chloride tablet comprised of polymer coated crystals of KCl which is orally administered to a patient requiring potassium supplementation which tablet provides for controlled release of the potassium chloride in the gastrointestinal tract and results in substantially less irritation to the gastric mucosa.

BACKGROUND OF THE INVENTION

It is well known that the administration of many diuretics increases the excretion of both sodium and potassium. The acute administration of such diuretics to a patient normally causes no problems. However, chronic administration of diuretics to the patient can result in the depletion of the potassium from the patient. For example, with patients having uncomplicated hypertension, the daily administration of diuretics produces a slight reduction in plasma potassium concentration. In edematous patients, the results are more variable. Some patients suffer from substantial depletion of potassium while others fail to show any evidence of depletion. There is a high incidence of severe potassium deficiency in patients treated simultaneously with diuretics and carbenoxolone which is an agent with mineralocorticoid activity.

As can be seen from the above discussion various treatments can result in potassium depletion, i.e., hypokalemia. Potassium depletion may be accompanied by a reduced tolerance to carbohydrates and a deficiency in glycogen deposition. Further, vasopressin-resistant polyuria is a prominent symptom. A deficit of potassium appears to increase the renal synthesis of prostaglandins, which in turn can decrease the permeability to water of the distal nephron and produce a diabetes insipidus-like syndrome.

When potassium is taken along with a normal diet it is slowly absorbed from the intestinal tract. Following distribution and uptake by the cells the kidneys excrete an appropriate amount to maintain a proper balance. As a consequence of the large volume of distribution and the rapid response of the kidney, the extracellular and intracellular concentrations of the ion are normally maintained within relatively narrow limits.

When potassium is administered as a drug, the factors that can govern the rate and extent of its distribution are of major importance. It is not possible to increase the total body content of potassium significantly above normal. However, it is very easy to raise the extracellular concentration excessively. It is the concentration in the extracellular fluid that determines life-threatening toxicity. Therefore, even though the administered potassium is eventually destined either to be excreted or taken up by the cells, knowledge of the transient concentration achieved in the plasma must govern the use of potassium as a therapeutic agent.

It is well known that large doses of potassium chloride taken orally can cause GI irritation, purging, weakness and circulatory disturbances. Since potassium depletion can cause problems for the patient as indicated above a controlled release formulation of potassium chloride which would replenish potassium in a controlled manner without the undesirable side effects is badly needed. In an attempt to meet the need of providing dosage units which can be used as potassium supplements a number of different dosage forms have been developed. For example U.S. Pat. No. 4,352,791 discloses a composition comprised of potassium and a therapeutically acceptable salicylate salt of salicylic acid. The composition is used in potassium therapy and is useful in some respects but does not provide sufficient protection with respect to preventing gastric ulcers.

U.S. Pat. No. 4,340,582 discloses an enteric coated erythromycin tablet and a water-soluble nontoxic salt in the core. This core may be potassium chloride.

U.S. Pat. No. 4,259,323 discloses a potassium chloride emulsion which includes various ingredients in an attempt to mask the bad taste of the potassium chloride. However, dosing compliance utilizing an emulsion often causes problems in that the emulsion may settle and the patient may take different amounts of the emulsion and/or different amounts of the KCl in a given amount of emulsion.

U.S. Pat. No. 4,259,315 discloses a controlled release potassium dosage form used in treating potassium deficiency. The dosage form is comprised of gelatin capsules which contain a mixture comprised of controlled release forms of micro encapsulated potassium salt and a hydrophilic surfactant.

Sugar-coated tablets containing potassium chloride in a wax matrix (non-enteric-coated) are marketed as a slowly available potassium source. Physicians Desk Reference (1979), page 794, states "fewer bowel lesions are observed with wax-matrix tablets compared to enteric-coated potassium chloride products, but that there have been reports of upper gastrointestinal bleeding associated with the wax-matrix tablets. Use of these wax-coated products should be discontinued immediately and the possibility of bowel obstruction or perforation considered if severe vomiting, abdominal pain, distention or gastrointestinal bleeding occurs." (See U.S. Pat. No. 4,259,315).

A slow release pharmaceutical composition is disclosed within U.S. Pat. No. 4,235,870. The composition is comprised of a combination of higher aliphatic alcohols and hydrated hydroxyalkyl cellulose in a ratio of 2:1 to 4:1 parts by weight. The composition is intended to provide slow release of the therapeutically active compound during a predetermined period of time of from 5 to 10 hours after oral administration of the composition. However, this composition tends to remain intact and does not disintegrate, thus producing high concentrations of KCl.

Others have used surfactants to improve dissolution rate of drugs when powders agglomerate and teach the rate of dissolution is proportional to the reduction in surface tension of the gastric juice (Remington's Pharmaceutical Sciences, 15th Ed. (1973) p. 297). Others have used surfactants such as Polysorbate 20 as an ingredient interior to microcapsules during preparation of microcapsules and have discussed the adverse effect of such agents on the increased release rate of solids from the microcapsules (Luzzi et al. J. Pharm. Sci. 56(9), 1174–7 (1967). (See U.S. Pat. No. 4,259,315).

The present inventors have found that the potassium chloride dosage forms presently available are not meeting all the needs of patients requiring potassium supplementation. Accordingly, the following invention was developed.

SUMMARY OF THE INVENTION

The present invention is a controlled release potassium chloride tablet. More specifically, the invention relates to a tablet which includes potassium chloride crystals which are coated with about 9.5 to 18% by weight of a polymeric mixture. The crystals preferably have a mesh size in the range of about 30 to 50 mesh and the coating is preferably comprised of from about 9.0 to about 15 parts by weight of ethylcellulose and about 0.5 to about 3.0 parts by weight hydroxypropylcellulose. The tablets also may include a compression aid; a disintegrant and a tableting lubricant.

A primary object of the present invention is to provide a controlled release potassium chloride tablet capable of being orally administered and safely replenishing potassium in a patient suffering from potassium depletion.

Another object of the present invention is to provide such a controlled release potassium chloride tablet which when administered orally minimizes adverse side effects such as GI irritation, purging, weakness and circulatory disturbances.

Still another object of the present invention is to provide such a controlled release potassium chloride tablet which acts as a safe electrolyte replenisher.

Another object of the present invention is to provide a safe method of treating patients suffering from potassium depletion.

Yet another object of the present invention is to provide a controlled release potassium chloride tablet which can be co-administered with a diuretic to a patient in a manner so as to prevent potassium depletion from the patient.

These and other objects of the invention will become apparent to those skilled in the art upon reading this disclosure.

DETAILED DESCRIPTION OF THE INVENTION

The essence of the present invention is a controlled release potassium chloride tablet. The active ingredient of the tablet is the salt potassium chloride and specifically the cation potassium. The potassium cation is preferably administered to the patient in such a manner so as to avoid side effects and prevent or relieve potassium depletion. The KCl tablets of the present invention may be co-administered with a diuretic.

The salt potassium chloride (KCl) occurs in nature as the mineral sylvine or sylvite. Various industrial preparations of potassium chloride exist. Further, there are numerous pharmaceutical potassium chloride preparations. The salt potassium chloride is a white crystal or crystalline powder having the following physical description: d 1.98. mp 773° C; 1 gram dissolves in 2.8 ml water; 1.8 ml boiling water; 14 ml glycerol; about 250ml alcohol; insoluble ether and acetone.

In accordance with the present invention potassium chloride crystals having a particle size distribution ranging from about 30 to about 50 mesh (about 0.59-0.29 mm), preferably about 40 mesh (about 0.37 mm), are utilized as "seed" crystals subjected to coating or microencapsulation and subsequently compressed into the tablet. In accordance with the present invention only minor amounts of the crystals would fall outside of the range disclosed above.

When the potassium chloride crystals having the size disclosed above are obtained they are then coated with a polymeric coating which includes ethylcellulose as a major component and hydroxypropylcellulose as a minor component. The weight ratio of the ethylcellulose to the hydroxypropylcellulose is at least 3.0. In accordance with the present invention it is contemplated that the weight ratio (ethylcellulose : hydroxypropylcellulose) can range from about 3.0:1 to about 30:1 with a preferred range being from about 5.0:1 to about 18:1, and still more preferably about 9:1. Hydroxypropylcellulose (molecular weight 60,000–1,000,000 preferably about 100,000) is sold under the trademark Klucel ® by Hercules. The hydroxypropyl cellulose may be replaced in whole or in part with polyethylene glycol, such as that sold under the trademark Carbowax ® by Union Carbide. Molecular weights of 200–8000 are useful, with 1000–6000 being preferred.

By providing the proper balance of the ethylcellulose to the hydroxypropylcellulose a polymer film can be formed on the seeds which will remain intact in the stomach (and afterwards) but which is permeable to gastric fluids, which dissolve and leach out the potassium chloride contained in the coated crystals (micro pellets). Further, these micro pellets will separate quickly upon reaching the stomach and thus avoid the accumulation of any large amount of KCl which could cause irritation.

The polymeric coating (combination of ethylcellulose and hydroxypropylcellulose) on the crystals makes up about 9.5 to about 18% of the total weight of the micro pellets and preferably about 13.3% of the weight of the micro pellets. Lesser amounts, that is, amounts below about 9% of the total weight of the micro pellets can cause the formation of bare spots on the potassium chloride crystals during the compression step, leading to undesirably rapid release of the potassium chloride in the body after oral administration. Increasing the amount of polymeric coating substantially above 18% can cause the potassium chloride to be released too slowly to be completely absorbed by the patient.

The present inventors have found it preferable to use a coating comprising ethylcellulose in an amount of about 9.0 to 15% by weight based on the total weight of the micro pellets, more preferably 11.9% by weight, and hydroxypropylcellulose in an amount of about 0.5 to 3.0%.

It is particularly preferred to use a higher molecular weight ethyl cellulose such as that designated as 100 and sold under the trademark Ethocel ® Standard Premium 100 or Ethocel ® Medium 100 by Dow Chemical. The use of higher molecular weight material like the 100 designation material limits breakage during compression. The numerical designations for ethylcellulose generally correspond to the viscosity of the product, with a higher numerical designation indicating a greater viscosity and higher molecular weight. The 100 designation corresponds to a viscosity of about 85–110 cp as measured in a 5% solution in an 80% toluene-20% ethanol solvent. The useful ethylcellulose designations are 7 and higher, corresponding to a viscosity of at least 6 cp, preferably more than 40 cp (designation 45 or higher) for crystals to be compressed into tablets. The ethoxyl content can be about 45–49.5%, preferably 45–46.5%. The present inventors determined that ethylcellulose 100 was preferred as compared with other ethylcellulose products as there is less breakage during compression. The lower viscosity ethylcelluloses, such as the type 10, are especially useful in making coated crystals for administration in capsules, when breakage from compression is not a problem.

Potassium chloride is normally provided in relatively large oral dosages in the range of 2 to 4 grams daily. Because of the large amount of the salt which is provided to the patient gastrointestinal irritation is common. This irritation can range from a slight discomfort to gastric ulcers. By including the crystals in the micro pellets in the manner indicated above and then compressing them in a conventional manner into tablets, the gastrointestinal irritation is alleviated or eliminated.

The individual crystals of potassium chloride having the mesh sizes indicated above are coated with the appropriate sustained release agents and compressed into tablets in a conventional manner. The tablets are coated and compressed in a manner so as to allow the tablets to disintegrate relatively quickly upon contact with an aqueous environment into the individual coated crystals, i.e., disintegration takes place in less than five minutes after oral administration.

The manufacturing process utilized applies a controlled and uniform coating permitting a more uniform dissolution as compared to a wax matrix and/or a coacervation formulation. Accordingly, the rapid disintegration and controlled dissolution of the tablets produced according the present invention permit the peristaltic motion of the gut to distribute the coated crystals over a wide surface area. Accordingly, concentrated quantities of potassium chloride do not come in contact with the GI mucosa, thus reducing the chances for gastric ulcers. This is one of the most important features of the present invention.

The importance of potassium supplement therapy has been well established. Physicians need products for the prevention of hypokalemia during chronic diuretic therapy. Compliance is essential for patients under going this type of therapy. The recommended dose in most patients is 40 mEq per day in divided doses. In accordance with currently approved labeling 20 mEq, or 2 doses having a size of 10 mEq should be taken twice daily in order to obtain a daily dose of 40 mEq. With the formulation provided by the present invention the tablet will include 20 mEq so that the recommended effective amount of potassium per single dose would not be altered. The daily dose would be achieved with one tablet twice daily thus facilitating compliance due to less individual units per dose. A 20 mEq tablet also presents to the physician a more palatable dosage form to the 20 mEq liquid therapy and an alternative to prescribing two tablets of the same sustained release formulation.

In severe cases of hypokalemia, higher doses (60-80 mEq) of potassium are required to reduce the loss of potassium during high dose diuretic therapy. In such cases, the physician would have available a safe higher strength tablet where, in his judgement, he is treating a patient with a compliance problem. Evidence exists that the tablet produced according to the present invention is non-irritating and non-toxic to the gastrointestinal tract.

The tablets produced in accordance with the present invention disintegrate into numerous sub-units when placed in water or placed on an aqueous food. After being disintegrated into the sub-units or micro pellets the potassium chloride of the present invention can be more easily administered to children and geriatric patients who often have difficulty in swallowing large tablets. The tablets can include conventional compression aids, e.g. microcrystalline cellulose, disintegrants, e.g. crospovidone, and lubricating agents, e.g. magnesium stearate.

Examples are prepared as indicated below:

EXAMPLE 1

The potassium chloride crystals (30-50 mesh) were coated in a 6" Wurster fluidized bed column with 15% (w/w) of Ethocel ® 10 and PEG 4500 E. (14:1 ratio). The Ethocel ® type 10 and PEG 4500 E were dissolved in chloroform and methanol co-solvent system (4:1 ratio). The crystals were coated at 60° C. inlet temperature. The spraying pressure was 1.5 bars and the spray speed was approximately 15ml per minute. Afterwards, 93% of the coated crystals, 6% of Avicel ® PH101 (microcrystalline cellulose) and 1% of crospovidone (cross-linked polyvinylpyrrolidone) were mixed well and compressed into tablets with a Stokes DS 3 press, equipped with capsule-shape punches (0.34"×0.873"×0.086"). The dosage of the tablets was 20 mEq or 1500 mg KCl.

A second batch of potassium chloride crystals was coated with 15% (w/w) of Ethocel ® type 100 and PEG 4500 E (14:1 ratio) and compressed into tablets which included the excipients indicated above. All the experimental procedures were the same as mentioned above, except the type of ethylcellulose used.

A dissolution study of the coated crystals (micro pellets) was performed in deionized water.

The following table is a summary of the dissolution test:

TABLE I

| | CUMULATIVE % KCl RELEASED | | | | |
|---|---|---|---|---|---|
| | 1 hr | 2 hr | 4 hr | 6 hr | Ethylcellulose Type |
| Coated Crystals | 17 | 35 | 63 | 85 | Ethocel ® 10 |
| Tablets | 46 | 63 | 83 | 96 | |
| Coated Crystals | 12 | 59 | 86 | 96 | Ethocel ® 100 |
| Tablets | 15 | 40 | 76 | 91 | |

EXAMPLE 2

The potassium chloride crystals (30-50 mesh size) were coated in a 6" Wurster fluidized bed column with 15% (w/w) of Ethocel ® 10, Klucel ® L.F. and Mg stearate (8.5:1:0.5 ratio). The Ethocel ® 10 and Klucel ® L.F. were dissolved in a chloroform and methanol co-solvent system. Magnesium stearate was then added to the polymer solution to form a suspension. The suspension was stirred by a lab stirrer throughout the coating process to avoid the sedimentation of magnesium stearate. The crystals were coated at 60° C. inlet temperature. The spraying pressure was 1.5 bars and the spray speed is approximately 15 ml per minute. Afterwards, 93% of the coated crystals, 6% of Avicel ® PH101 (microcrystalline cellulose) and 1% of crospovidone (crosslinked polyvinylpyrrolidone) are mixed well and compressed into capsule-shaped tablets. The dosage of the tablets was 20 mEq or 15 mg of KCl.

A second batch of potassium chloride crystals was coated with 15% (w/w) of Ethocel ® 100, Klucel ® L.F. and magnesium stearate (8.5:1:0.5 ratio) and compressed into tablets with the same excipients indicated above. All the experimental procedures were the same as mentioned above except the type of ethylcellulose used.

A dissolution study of the coated crystals and tablets was performed in deionized water.

The following table is a summary of the dissolution test:

TABLE II

| | CUMULATIVE % KCl RELEASED | | | | |
|---|---|---|---|---|---|
| | 1 hr | 2 hr | 4 hr | 6 hr | Ethocel ® Type |
| Coated Crystals | 33 | 52 | 78 | 94 | Ethocel ® 10 |
| Tablets | 52 | 69 | 86 | 97 | |
| Coated Crystals | 27 | 59 | 84 | 95 | Ethocel ® 100 |
| Tablets | 26 | 55 | 83 | 94 | |

In accordance with a preferred embodiment of the present invention potassium chloride tablets containing 1500mg of potassium chloride are prepared. The potassium crystals form about 68% to about 86.5% by weight of these tablets and are coated with ethylcellulose (preferably Ethocel ® 100) in an amount in the range of 9 to 15% by weight based on the weight of the micro pellets formed with the potassium chloride crystals; 0.5 to 3% by weight of hydroxypropylcellulose based on the weight of the micro pellets; 0.5 to 2% by weight of magnesium stearate based upon the weight of the tablet; 3 to 10% by weight of microcrystalline cellulose based upon the weight of the tablet; 0.5 to 2% by weight crospovidone based upon the weight of the tablet.

Within each of these ranges it is particularly preferred for the 1500 mg tablets to include 79 weight percent of potassium chloride, 11.9% by weight of ethylcellulose (preferably Ethocel ® 100), 1.4% by weight hydroxypropylcellulose, 0.7% by weight of magnesium stearate, 6% by weight of microcrystalline cellulose and 1% by weight of crospovidone.

In accordance with the present invention a clinical batch of 1500 mg tablets of potassium chloride were prepared. The tablets were comprised as shown in the following Table III.

TABLE III

POTASSIUM CHLORIDE S.R. TABLETS
20 mEq
QUANTITATIVE LIST OF COMPONENTS

| QUANTITY/ TABLETS | | INGREDIENTS | QUANTITY/ BATCH | % WT. |
|---|---|---|---|---|
| (20 mEq) 1500 | mg | Potassium Chloride, USP | 255.00 kg | 79.0 |
| 225 | mg | Ethylcellulose, NF (Ethocel ®, Type 100) | 38.25 kg | 11.9 |
| 27 | mg | Hydroxypropylcellulose, NF (Klucel ®, L.F.) | 4.50 kg | 1.4 |
| 13 | mg | Magnesium Stearate, NF | 2.25 kg | 0.7 |
| 114 | mg | Microcrystalline Cellulose, NF (Avicel ® PH 101) | 19.36 kg | 6.0 |
| 19 | mg | Crospovidone, NF (Polyplasdone XL) | 3.23 kg | 1.0 |
| | * | Methyl Alcohol, NF (Methanol) | 168.65 kg | * |
| | * | Methylene Chloride, NF | 846.45 kg | * |
| 1898 | mg | TOTALS | 322.59 kg/ 170,000 Tablets | |

* Removed during processing.

COMPARATIVE EXPERIMENT

In order to demonstrate the safety of the present invention, a clinical study was carried out which compared potassium chloride tablets (20 mEq) produced in accordance with the present invention with four commercial products as follows: Slow-K ® (a sugar-coated wax matrix tablets from Ciba); Micro-K Extencaps ®, (capsules of crystalline KCl particles coated with polymer from A. H. Robins); Kaon ® Elixir (liquid potassium gluconate), and placebo.

In this particular investigator blinded study comparing the 20 mEq KCl tablets to 4 standard preparations in a dose of 80 mEq per day, no serious endoscopic lesions were found with the tablet of the present invention. Overall, the safety of the tablet was equal to or better than any of the comparative agents.

The present invention has been disclosed and described herein in what is considered to be its most preferred embodiments. It should be noted that variations may occur to those skilled in the art upon reading the present disclosure and that such variations are intended to come within the scope of the present invention.

What is claimed is:

1. A pharmaceutical dosage unit in tablet form for oral administration of potassium chloride, comprising;
   a plurality of coated potassium chloride crystals, the amount of potassium chloride being in the range of about 64% to about 86.5% by weight based on the total weight of the dosage unit;
   a coating material for the individual potassium chloride crystals, the coating material comprising ethylcellulose in the amount in the range of about 9% to about 15% by weight based on the total weight of the coated crystals and at least one member selected from hydroxypropylcellulose and polyethylene glycol in an amount in the range of about 0.5% to about 3% by weight based on the total weight of the coated crystals and said ethylcellulose has a viscosity greater than 40 cp.

2. A pharmaceutical dosage unit as claimed in claim 1, wherein the tablet is further comprised of magnesium stearate in an amount in the range of about 0.5% to 2.0% by weight based on the total weight of the tablet.

3. A pharmaceutical dosage unit as claimed in claim 2, wherein the tablet is further comprised of a microcrystalline cellulose in an amount in the range of about 3 to 10% by weight based on the total weight of the tablet.

4. A pharmaceutical dosage unit as claimed in claim 3, further comprising cross-linked polyvinylpyrolidone in an amount in the range of about 0.5 to about 2.0% by weight based on the total weight of the tablet.

5. A pharmaceutical dosage unit as claimed in claim 1, wherein the potassium chloride is in the form of crystals which have a mesh size in the range of about 30 to about 50 mesh.

6. A pharmaceutical dosage unit as claimed in claim 5, wherein the potassium chloride crystals have a mesh size of about 40 mesh.

7. A pharmaceutical dosage unit as claimed in claim 1, wherein the ethylcellulose has a viscosity of from 85 to 110 cp.

8. A pharmaceutical dosage unit as claimed in claim 1, wherein the member selected from hydroxypropylcellulose and polyethylene glycol is hydroxypropylcellulose.

9. A pharmaceutical unit as claimed in claim 1, wherein the member selected from hydroxypropylcellulose and polyethylene glycol is polyethylene glycol.

10. A method of providing potassium to a subject in need of potassium, comprising administering to the subject a therapeutically useful amount of potassium chloride in a dosage unit according to claim 1.

11. The method of claim 10, wherein the dosage unit is disintegrated in water or on an aqueous food prior to administration.

12. The pharmaceutical dosage unit in tablet form of claim 2 comprising:
68–86.5% by weight of coated potassium chloride crystals;
0.5–3% by weight of magnesuim stearate;
3–15% by weight of microcrystalline cellulose;
0.5–2.0% by weight cross-linked polyvinyl pyrrolidone;
wherein the individual potassium chloride crystals are coated with a material comprising ethyl cellulose in an amount in the range of about 9% to about 15% by weight based on the total weight of the coated crystals and at least one member selected from hydroxypropylcellulose and polyethlene glycol in an amount in the range of about 0.5% to about 3% by weight based on the total weight of the coated crystals.

* * * * *

UNITED STATES PATENT AND TRADEMARK OFFICE
CERTIFICATE OF CORRECTION

PATENT NO. : 4,863,743

DATED : September 5, 1989

INVENTOR(S) : Charles Hsiao and Chi T. Chou

It is certified that error appears in the above-identified patent and that said Letters Patent are hereby corrected as shown below:

Column 8, line 22: "64%" should read --68%--
Column 10, line 7: "claim 2" should read --claim 1--
Column 10, line 10: "0.5-3%" should read --0.5-2%--
Column 10, line 10: "magnesuim" should read --magnesium--
Column 10, line 11: "3-15%" should read --3-10%--

Signed and Sealed this

Eighth Day of October, 1996

Attest:

BRUCE LEHMAN

*Attesting Officer*     *Commissioner of Patents and Trademarks*